(12) United States Patent
Hirano et al.

(10) Patent No.: US 8,314,085 B2
(45) Date of Patent: Nov. 20, 2012

(54) AGENT FOR OVERCOMING RESISTANCE TO ANTI-CANCER AGENT

(75) Inventors: Masuharu Hirano, Saitama (JP); Tomio Yamakawa, Chiba (JP); Toshihisa Ishikawa, Kanagawa (JP); Hikaru Saito, Kanagawa (JP)

(73) Assignee: Nippon Chemiphar Co., Ltd., Chiyoda-ku, Tokyo (JP)

( * ) Notice: Subject to any disclaimer, the term of this patent is extended or adjusted under 35 U.S.C. 154(b) by 12 days.

(21) Appl. No.: 13/169,670

(22) Filed: Jun. 27, 2011

(65) Prior Publication Data

US 2011/0257201 A1 Oct. 20, 2011

Related U.S. Application Data

(63) Continuation of application No. 12/305,809, filed as application No. PCT/JP2007/063062 on Jun. 22, 2007, now abandoned.

(30) Foreign Application Priority Data

Jun. 22, 2006 (JP) ................................ 2006-172290

(51) Int. Cl.
*A61K 31/33* (2006.01)

(52) U.S. Cl. ...................................................... 514/183

(58) Field of Classification Search .................... 514/183
See application file for complete search history.

(56) References Cited

U.S. PATENT DOCUMENTS

2007/0293512 A1 12/2007 Yoshida et al.

FOREIGN PATENT DOCUMENTS

WO WO 2005-121153 A1 12/2005

OTHER PUBLICATIONS

Smalley et al., "Allopurinol: Intravenous Use for Prevention and Treatment of Hyperuricemia", Journal of Clinical Oncology, 18(8), pp. 1758-1763, 2000.

*Primary Examiner* — Brandon J Fetterolf
*Assistant Examiner* — Christopher R Stone
(74) *Attorney, Agent, or Firm* — Nixon Peabody LLP; Jeffrey L. Costellia

(57) ABSTRACT

An agent comprising, as an active ingredient, a xanthine oxidase inhibitor such as 2-[3-cyano-4-(4-fluorophenoxy) phenyl]-4-hydroxythiazolo[5,4-d]pyrimidine potassium salt, 2-[3-cyano-4-(4-fluorophenoxy)phenyl]thiazolo[5,4-d]pyrimidine, 2-(3-cyano-4-phenoxyphenyl)-4-hydroxythiazolo[5, 4-d]pyrimidine, 2-(3-cyano-4-phenoxyphenyl)-4-hydroxythiazolo[5,4-d]pyrimidine potassium salt, 2-(3-cyano-4-phenoxyphenyl)thiazolo[5,4-d]pyrimidine, TMX-67, and FYX-051, which can be used as an agent for overcoming anti-cancer agent resistance.

7 Claims, No Drawings

AGENT FOR OVERCOMING RESISTANCE TO ANTI-CANCER AGENT

TECHNICAL FIELD

The present invention relates to an agent containing a xanthine oxidase inhibitor as an active ingredient for overcoming anti-cancer agent resistance.

PRIOR ART

Chemotherapy is indispensable for cancer treatment. On the other hand, cancer often develops resistance to chemotherapy. Once a cancer cell acquires resistance to a anti-cancer agent, the cell frequently shows resistance to another anti-cancer agent unused in treatment or multiple drugs having different action mechanisms or different structures, which is said to be multidrug resistance. Resistance is an enormous problem in treatment, and multidrug resistance is a particularly serious problem. It has been desired to develop an agent for overcoming multidrug resistance. One mechanism of multidrug resistance is overexpression of ABC transporters such as P-glycoprotein (ABCB1) and MRP1 (ABCC1), which are localized in cell membrane. The ABC transporters excrete intracellular substrates of various structures (such as agents, physiologically active substances) out of cells in an ATP-dependent manner. Therefore, overexpression of them decreases intracellular concentrations of the drugs to cause resistance to various drugs such as anti-cancer agent.

Breast Cancer Resistance Protein (BCRP/ABCG2) has recently been identified as an ABC transporter (Doyle L A et al.: Proc Natl Acad Sci USA., 95:15665-15670 (1998); Allikmets R et al.: Cancer Res., 58:5337-5339 (1998); and Miyake K et al.: Cancer Res., 59:8-13 (1999)).

BCRP excretes SN-38, which is an active metabolite of irinotecan, or anti-cancer agents such as mitoxantrone and topotecan out of cells. Therefore, BCRP has been noted as a molecular target to overcome anti-cancer agent resistance (cf., JP 2003-63989 A).

It has been known that the compound having a condensed dicyclic heterocyclic ring represented by the below-mentioned formula (I) or (II) has xanthine oxidase (XOD) inhibitory action (cf., WO 2005/121153 A1, WO 2003/042185 A1, WO 2007/004688 A1).

Febuxostat (TMX-67) and 4-[5-pyridin-4-yl-1H-[1,2,4]triazol-3-yl]pyridine-2-carbonitrile (FYX-051) have xanthine oxidase inhibitory action. They are available agents for treating hyperuricemia.

However, it has not been known that the compound represented by the below-mentioned formula (I) or (II), TMX-67 or the like has BCRP inhibitory action.

DISCLOSURE OF INVENTION

An object of the invention is to provide an agent for overcoming drug resistance or an agent for overcoming anti-cancer agent resistance.

The present inventors have discovered that the compound represented by the below-mentioned formula (I) or (II), TMX-67 or the like, which has xanthine oxidase inhibitory action, also has BCRP inhibitory action. The present invention has been completed based on the discovery.

The present invention resides in an agent containing a compound having the following formula (I) or a salt thereof as an active ingredient for overcoming drug resistance:

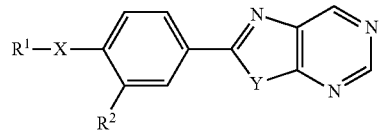

wherein $R^1$ is $C_{2-8}$ alkenyl, $C_{6-10}$ aryl, or heteroaryl in which the aryl and heteroaryl can have a substituent selected from the group consisting of $C_{1-8}$ alkyl, $C_{1-8}$ alkyl substituted with halogen, $C_{1-8}$ alkoxy, $C_{1-8}$ alkoxy substituted with halogen, $C_{2-8}$ alkoxycarbonyl, formyl, carboxyl, halogen, hydroxyl, nitro, cyano, amino, $C_{6-10}$ aryl, and $C_{6-10}$ aryloxy;

$R^2$ is cyano, nitro, formyl, carboxyl, carbamoyl, or $C_{2-8}$ alkoxycarbonyl;

X is oxygen, —N($R^3$)—, or —S(O)$_n$—, and $R^3$ is a hydrogen, $C_{1-8}$ alkyl, or the group mentioned above for $R^1$, or $R^1$ and $R^3$ are combined to form morpholinyl, thiomorpholinyl, or piperazinyl, and n is an integer of 0 to 2; and Y is oxygen, sulfur, or NH.

The invention also resides in an agent containing a compound having the following formula (II) or a salt thereof as an active ingredient for overcoming drug resistance:

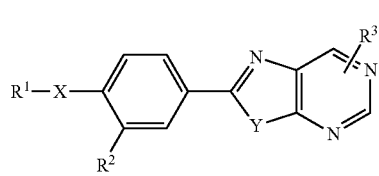

wherein $R^1$ is $C_{6-10}$ aryl or heteroaryl in which the aryl and heteroaryl can have a substituent selected from the group consisting of $C_{1-8}$ alkyl, $C_{1-8}$ alkyl substituted with halogen, $C_{1-8}$ alkoxy, $C_{1-8}$ alkoxy substituted with $C_{1-8}$ alkoxy, $C_{2-8}$ alkoxycarbonyl, formyl, carboxyl, halogen, hydroxyl, nitro, cyano, amino, $C_{6-10}$ aryl, and $C_{6-10}$ aryloxy;

$R^2$ is cyano, nitro, formyl, carboxyl, carbamoyl, or $C_{2-8}$ alkoxycarbonyl;

$R^3$ is hydroxyl, amino, carboxyl, mercapto, $OR^4$, or $NHR^5$, and each of $R^4$ and $R^5$ is $C_{1-8}$ alkyl or $C_{1-8}$ alkyl substituted with a group or atom selected from the group consisting of halogen, hydroxyl, nitro, cyano, amino, $C_{6-10}$ aryl, and $C_{6-10}$ aryloxy;

X is oxygen, —N($R^6$)—, or —S(O)$_n$—, and $R^6$ is a hydrogen, $C_{1-8}$ alkyl, or the group mentioned above for $R^1$, and n is an integer of 0 to 2; and Y is oxygen or sulfur.

The invention also resides in an agent containing Febuxostat or 4-[5-pyridin-4-yl-1H-[1,2,4]triazol-3-yl]pyridine-2-carbonitrile as an active ingredient for overcoming drug resistance.

The present invention further resides in an agent containing a compound having the above-mentioned formula (I) or a salt thereof as an active ingredient for overcoming anti-cancer agent resistance.

The invention also resides in an agent containing a compound having the following formula (II) or a salt thereof as an active ingredient for overcoming anti-cancer agent resistance.

The invention furthermore resides in an agent containing Febuxostat or 4-[5-pyridin-4-yl-1H-[1,2,4]triazol-3-yl]pyridine-2-carbonitrile as an active ingredient for overcoming anti-cancer agent resistance.

The invention also resides in a therapeutic composition against a cancer cell of multidrug resistance, wherein the composition comprises an anti-cancer agent and a compound selected from the group consisting of 2-(3-cyano-4-phenoxyphenyl)thiazolo[5,4-d]pyrimidine, 2-[3-cyano-4-(4-fluorophenoxy)phenyl]thiazolo[5,4-d]pyrimidine, 2-(3-cyano-4-phenoxyphenyl)-4-hydroxythiazolo[5,4-d]pyrimidine, potassium salt of 2-(3-cyano-4-phenoxyphenyl)-4-hydroxythiazolo[5,4-d]pyrimidine, and potassium salt of 2-[3-cyano-4-(4-fluorophenoxy)phenyl]-4-hydroxythiazolo[5,4-d]pyrimidine, Febuxostat and 4-[5-pyridin-4-yl-1H-[1,2,4]triazol-3-yl]pyridine-2-carbonitrile.

BEST EMBODIMENTS OF INVENTION

The present invention is described below in more detail.

The compound described in the formula (I) can be prepared according to methods described in the above-mentioned WO 2005/121153 A1, WO 2003/042185 A1, WO 2007/004688 A1 and the below-mentioned reference examples.

The compound described in the formula (I) preferably is a compound described below or a salt thereof.

(1-1) A compound having the above-mentioned formula (I) or a salt thereof, wherein $R^1$ is phenyl, naphthyl, furyl, pyrrolyl, thienyl, piperidyl, pyrimidinyl, pyranyl, pyridyl, thiazolyl, imidazolyl, indolyl, or quinolyl in which the phenyl, naphthyl, furyl, pyrrolyl, thienyl, piperidyl, pyrimidinyl, pyranyl, pyridyl, thiazolyl, imidazolyl, indolyl, and quinolyl can have a substituent selected from the group consisting of $C_{1-8}$ alkyl, $C_{1-8}$ alkyl substituted with halogen, $C_{1-8}$ alkoxy, $C_{1-8}$ alkoxy substituted with halogen, $C_{2-8}$ alkoxycarbonyl, formyl, carboxyl, halogen, hydroxyl, nitro, cyano, amino, $C_{6-10}$ aryl, and $C_{6-10}$ aryloxy (1-2) A compound having the above-mentioned formula (I) or a salt thereof, wherein $R^1$ is phenyl or pyridyl in which the phenyl and pyridyl can have a substituent selected from the group consisting of $C_{1-8}$ alkyl, $C_{1-8}$ alkyl substituted with halogen, $C_{1-8}$ alkoxy, $C_{1-8}$ alkoxy substituted with halogen, $C_{2-8}$ alkoxycarbonyl, formyl, carboxyl, halogen, hydroxyl, nitro, cyano, amino, $C_{6-10}$ aryl, and $C_{6-10}$ aryloxy (1-3) A compound having the above-mentioned formula (I) or a salt thereof, wherein $R^1$ is phenyl or pyridyl in which the phenyl and pyridyl can have a substituent selected from the group consisting of $C_{1-8}$ alkyl, $C_{1-8}$ alkyl substituted with halogen, $C_{1-8}$ alkoxy, carboxyl, halogen, hydroxyl, nitro, cyano, and amino (1-4) A compound having the above-mentioned formula (I), a compound defined in one of (1-1) to (1-3), or a salt thereof, wherein $R^2$ is cyano or nitro (1-5) A compound having the above-mentioned formula (I), a compound defined in one of (1-1) to (1-3), or a salt thereof, wherein $R^2$ is cyano (1-6) A compound having the above-mentioned formula (I), a compound defined in one of (1-1) to (1-5), or a salt thereof, wherein X is oxygen, NH, or sulfur (1-7) A compound having the above-mentioned formula (I), a compound defined in one of (1-1) to (1-5), or a salt thereof, wherein X is oxygen or sulfur (1-8) A compound having the above-mentioned formula (I), a compound defined in one of (1-1) to (1-7), or a salt thereof, wherein Y is sulfur or NH (1-9) A compound having the above-mentioned formula (I), a compound defined in one of (1-1) to (1-7), or a salt thereof, wherein Y is sulfur (1-10) A compound having the above-mentioned formula (I) or a salt thereof, wherein $R^1$ is phenyl or pyridyl in which the phenyl and pyridyl can have a substituent selected from the group consisting of $C_{1-8}$ alkyl, $C_{1-8}$ alkyl substituted with halogen, $C_{1-8}$ alkoxy, carboxyl, halogen, hydroxyl, nitro, cyano, and amino; $R^2$ is cyano or nitro; X is oxygen or sulfur; and Y is sulfur or NH (1-11) A compound having the above-mentioned formula (I) or a salt thereof, wherein $R^1$ is phenyl or pyridyl in which the phenyl and pyridyl can have a substituent selected from the group consisting of $C_{1-8}$ alkyl, $C_{1-8}$ alkyl substituted with halogen, $C_{1-8}$ alkoxy, carboxyl, halogen, hydroxyl, nitro, cyano, and amino; $R^2$ is cyano or nitro; X is oxygen or sulfur; and Y is sulfur (1-12) A compound having the above-mentioned formula (I) or a salt thereof, wherein $R^1$ is phenyl or pyridyl in which the phenyl and pyridyl can have a substituent selected from the group consisting of $C_{1-8}$ alkyl, $C_{1-8}$ alkyl substituted with halogen, $C_{1-8}$ alkoxy, carboxyl, halogen, hydroxyl, nitro, cyano, and amino; $R^2$ is cyano or nitro; X is oxygen; and Y is sulfur (1-13) 2-(3-Cyano-4-phenoxyphenyl)thiazolo[5,4-d]pyrimidine and 2-[3-cyano-4-(4-fluorophenoxy)phenyl]thiazolo[5,4-d]pyrimidine (which are particularly preferred)

WO 2005/121153 A1 discloses a process for preparation of the compound described in the formula (II).

The compound described in the formula (II) preferably is a compound described below or a salt thereof.

(2-1) A compound having the above-mentioned formula (II) or a salt thereof, wherein $R^1$ is phenyl, naphthyl, furyl, pyrrolyl, thienyl, imidazolyl, pyrimidinyl, thiazolyl, pyridyl, indolyl, or quinolyl in which the phenyl, naphthyl, furyl, pyrrolyl, thienyl, imidazolyl, pyrimidinyl, thiazolyl, pyridyl, indolyl, and quinolyl can have a substituent selected from the group consisting of $C_{1-8}$ alkyl, $C_{1-8}$ alkyl substituted with halogen, $C_{1-8}$ alkoxy, $C_{2-8}$ alkoxycarbonyl, formyl, carboxyl, halogen, hydroxyl, nitro, cyano, amino, $C_{6-10}$ aryl, and $C_{6-10}$ aryloxy (2-2) A compound having the above-mentioned formula (II) or a salt thereof, wherein $R^1$ is phenyl which can have a substituent selected from the group consisting of $C_{1-8}$ alkyl, $C_{1-8}$ alkyl substituted with halogen, $C_{1-8}$ alkoxy, $C_{2-8}$ alkoxycarbonyl, formyl, carboxyl, halogen, hydroxyl, nitro, cyano, amino, $C_{6-10}$ aryl, and $C_{6-10}$ aryloxy (2-3) A compound having the above-mentioned formula (II) or a salt thereof, wherein $R^1$ is phenyl which can have a substituent selected from the group consisting of $C_{1-8}$ alkyl, $C_{1-8}$ alkyl substituted with halogen, $C_{3-8}$ alkoxy, $C_{2-8}$ alkoxycarbonyl, formyl, carboxyl, halogen, phenyl, and phenoxy (2-4) A compound having the above-mentioned formula (II), a compound defined in one of (2-1) to (2-3), or a salt thereof, wherein $R^2$ is cyano or nitro (2-5) A compound having the above-mentioned formula (II), a compound defined in one of (2-1) to (2-3), or a salt thereof, wherein $R^2$ is cyano (2-6) A compound having the above-mentioned formula (II), a compound defined in one of (2-1) to (2-5), or a salt thereof, wherein $R^3$ is hydroxyl (2-7) A compound having the above-mentioned formula (II), a compound defined in one of (2-1) to (2-6), or a salt thereof, wherein the substitution position of $R^3$ is 4-position of condensed (dicyclic) heterocyclic ring (2-8) A compound having the above-mentioned formula (II), a compound defined in one of (2-1) to (2-7), or a salt thereof, wherein X is oxygen, NH, or sulfur (2-9) A compound having the above-mentioned formula (II), a compound defined in one of (2-1) to (2-7), or a salt thereof, wherein X is oxygen (2-10) A compound having the above-mentioned formula (II), a compound defined in one of (2-1) to (2-9), or a salt thereof, wherein Y is sulfur (2-12) 2-(3-cyano-4-phenoxyphenyl)-4-hydroxythiazolo[5,4-d]pyrimidine, potassium salt of 2-(3-cyano-4-phenoxyphenyl)-4-hydroxythiazolo[5,4-d]pyrimidine, and potassium salt of 2-[3-cyano-4-(4-fluorophenoxy)phenyl]-4-hydroxythiazolo[5,4-d]pyrimidine (which are particularly preferred active ingredients)

The agent of the present invention for overcoming resistance is intended for anti-cancer agents such as irinotecan, SN-38, which is an active metabolite of irinotecan, mitoxantrone, topotecan, methotrexate, doxorubicin, daunorubicin, etoposide, gefitinib, and imatinib.

There is no specific limitation on kinds of cancers targeted with the agent of the present invention for overcoming anti-cancer agent resistance, so long as the cancers overexpressing BCRP. Examples of cancers with resistance include blood cancer (hematological malignancy), liver cancer, colon cancer, lung cancer, breast cancer, ovarian cancer, cervical cancer, osteosarcoma, brain tumor, pancreatic cancer, and prostate cancer.

The pharmacological effects of the invention are described below.

Below-described Example 1 is an experiment confirming an effect of compounds on BCRP-mediated methotrexate transport.

As is evident from Table 1, it has been confirmed that each of the compound 1 (potassium salt of 2-[3-cyano-4-(4-fluorophenoxy)phenyl]-4-hydroxythiazolo[5,4-d]pyrimidine), the compound 2 (2-[3-cyano-4-(4-fluorophenoxy)phenyl] thiazolo[5,4-d]pyrimidine), the compound 3 (potassium salt of 2-(3-cyano-4-phenoxyphenyl)-4-hydroxythiazolo[5,4-d] pyrimidine), the compound 4 (2-(3-cyano-4-phenoxyphenyl) thiazolo[5,4-d]pyrimidine), TMX-67, and FYX-051 strongly inhibits BCRP-mediated methotrexate transport.

Below described Example 2 is an experiment confirming an effect of compounds on anti-cancer agent resistance in BCRP-overexpressing cells (Flp-In-293/BCRP).

Each of the compounds 1 and 2 reverses resistance of Flp-In-293/ABCG2 cells to SN-38 in a concentration-dependent manner. The compound 1 and the compound 2 reversed the resistance by about 96% and about 90% respectively at the concentration of 5 µmol/L. Further, the compounds do not affect viability of Flp-In-293/ABCG2 cells up to the examined concentration of 10 µmol/L. Therefore, it has been confirmed that the compounds 1 and 2 exhibit effect of overcoming anti-cancer agent resistance in BCRP-overexpressing cells without exhibiting toxicity to the cells. In addition, in the experiments conducted in the same manner as in Example 2, the compound 5 (2-(3-cyano-4-phenoxyphenyl)-4-hydroxythiazolo[5,4-d]pyrimidine), TMX-67, and FYX-051 do not exhibit toxicity to the cells at the concentration of 10 µmol/L, and each of them reversed the resistance by about 96%, about 82% and about 39% respectively at the concentration of 5 µmol/L.

On the other hand, among the known agents having xanthine oxidase (XOD) inhibitory action, allopurinol and oxypurinol do not have an inhibitory action on BCRP-mediated methotrexate transport, and do not exhibit an effect of overcoming resistance to SN-38. Further, Y-700 (1-[3-cyano-4-(2,2-dimethylpropoxy)phenyl]-1H-pyrazole-4-carboxylic acid) also does not exhibit an effect of overcoming resistance to SN-38 (Comparison example 1 and 2).

As is described above, the agent having xanthine oxidase (XOD) inhibitory action, particularly the compound represented by the above-mentioned formula (I) or (II), TMX-67, or FYX-051 can be used as an active ingredient for overcoming drug resistance, particularly as an active ingredient for overcoming anti-cancer agent resistance.

The agent for overcoming drug resistance or the agent for overcoming anti-cancer agent resistance of the invention can be administered to human by ordinary administration methods such as oral administration or parenteral administration.

The agent can be granulated in ordinary manners for the preparation of pharmaceuticals. For instance, the agent can be processed to give pellets, granule, powder, capsule, suspension, injection, suppository, and the like.

For the preparation of these pharmaceuticals, ordinary additives such as vehicles, disintegrators, binders, lubricants, dyes, and diluents can be used. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpyrrolidone (PVP) as the binders.

The agent of the invention can be administered to an adult generally in an amount of 0.1 mg to 100 mg a day by parenteral administration and 1 mg to 2,000 mg a day by oral administration. The dosage can be adjusted in consideration of age and conditions of the patient.

A therapeutic agent (composition) comprising an agent for overcoming anti-cancer agent resistance and a known anti-cancer agent can be prepared according to a preparation method of a conventional composition. The two agents can also separately be administered to a patient at the same time or at some intervals.

In case of hematological malignancy, solid tumor with metastasis and the like, the administration of anti-cancer agent induces abrupt tumor necrosis resulting in the release of a large amount of the intracellular components of the tumor cells into blood. As a result, hyperuricemia, hyperkalemia, or hypocalcemia occurs and these symptoms sometimes induce renal failure or cardiac arrest (tumor lysis syndrome). The active ingredient of the invention has xanthine oxidase inhibitory action as well as effect of overcoming anti-cancer agent resistance. Therefore, the ingredient of the invention is also effective in treating hyperurcemia caused with tumor lysis.

The invention is further described by the following examples, but is not limited to these examples.

EXAMPLES

Reference Example 1

(1) 4-Chloro-N-(4-chloro-5-pyrimidinyl)-3-cyanobenzamide

4-Chloro-3-cyanobenzoic acid (7.01 g, 38.6 mmol) was suspended in benzene (70 mL). Thionyl chloride (3.6 mL, 49.6 mmol) was added to the suspension, and the mixture was refluxed with heating for 4 hours. The reaction liquid was condensed under reduced pressure. 5-Amino-4-chloropyrimidine (5.00 g, 38.6 mmol), dichloromethane (70 mL), and pyridine (3.6 mL, 44.5 mmol) were added to the obtained acid chloride. The mixture was stirred at room temperature for 7 hours. Chloroform (50 mL) and water (50 mL) was added to the reaction solution to filtrate crystals. The obtained crystals were washed with chloroform (20 mL) and water (20 mL), and air-dried to obtain 7.35 g (yield: 65%) of the subject compound as white crystals. Further, 0.62 g (yield: 8%) of the subject compound was obtained from a mixed solution of mother liquid and washings as pale brown crystals (secondary crystals). The total yield was 73%.

mp: 189-190° C.

¹H NMR (CDCl₃, 400 MHz): δ=7.74 (1H, d, J=8 Hz), 8.07 (1H, dd, J=2 Hz, 8 Hz), 8.13 (1H, s), 8.23 (1H, d, J=2 Hz), 8.83 (1H, s), 9.79 (1H, s).

(2) 2-(4-Chloro-3-cyanophenyl)thiazolo[5,4-d]pyrimidine

The above-obtained 4-chloro-N-(4-chloro-5-pyrimidinyl)-3-cyanobenzamide (7.98 g, 27.2 mmol) and Lawesson's reagent (8.25 g, 20.4 mmol) were suspended in toluene (150 mL). The suspension was refluxed with heating for 8 hours, and cooled to room temperature to filtrate precipitated crystals. The crystals were washed with chloroform (75×2), and air-dried to obtain 7.25 g (yield: 98%) of the subject compound as pale yellow crystals.

mp: 278-280° C. (decomposition)
¹H NMR (DMSO-d₆, 400 MHz): δ=7.99 (1H, d, J=9 Hz), 8.47 (1H, dd, J=2 Hz, 9 Hz), 8.70 (1H, d, J=2 Hz), 9.20 (1H, s), 9.54 (1H, s).

(3) 2-[3-Cyano-4-(4-fluorophenoxy)phenyl]thiazolo[5,4-d]pyrimidine

4-Fluorophenol (383 mg, 3.42 mmol) was added to a suspension of 55% sodium hydride (150 mg, 3.44 mmol) and dried DMSO (7 ml). The mixture was stirred at 50° C. for 30 minutes. The above-mentioned 2-(4-chloro-3-cyanophenyl)thiazolo[5,4-d]pyrimidine (776 mg, 2.85 mmol) was added to the reaction liquid. The mixture was stirred at 50° C. for 4 hours, and cooled to room temperature. Water (35 mL) was added to the reaction liquid to filtrate precipitated crystals. The crystals were washed with water (20 mL), and air-dried. The obtained crystals were purified by a silica gel column chromatography (chloroform), washed with ether (15 mL), and dried to obtain 701 mg (yield: 71%) of the subject compound as pale yellow crystals.

mp: 175-177° C.
¹H NMR (CDCl₃, 400 MHz): δ=6.94 (1H, d, J=9 Hz), 7.1-7.2 (4H, m), 8.18 (1H, dd, J=2 Hz, 9 Hz), 8.44 (1H, d, J=2 Hz), 9.13 (1H, s), 9.35 (1H, s).
IR (KBr) cm⁻¹: 2233, 1606, 1564, 1419, 1300, 1119, 1011, 916, 893, 847, 829, 777, 760, 758, 723, 702, 700, 650, 648, 597, 526, 496, 490.
FAB-MS (m/e): 349 (M+1)

Reference Example 2

2-(3-Cyano-4-phenoxyphenyl)thiazolo[5,4-d]pyrimidine

Phenol (45 mg, 0.48 mmol) was added to a suspension of 55% sodium hydride (23 mg, 0.53 mmol) and dried DMSO (1 mL). The mixture was stirred at room temperature for 30 minutes. The above-mentioned 2-(4-chloro-3-cyanophenyl)thiazolo[5,4-d]pyrimidine (120 mg, 0.44 mmol) was added to the reaction liquid. The mixture was stirred at 60° C. for 4 hours, and cooled to room temperature. Water (5 mL) was added to the reaction liquid to filtrate precipitated crystals. The crystals were washed with water (5 mL), ethanol (1 mL), and then ether (2 mL) in the order. The crystals were dried at room temperature under reduced pressure to obtain 100 mg (yield: 69%) of the subject compound as pale brown crystals.

mp: 154-156° C.
¹H NMR (DMSO-d₆, 400 MHz): δ=7.08 (1H, d, J=9 Hz), 7.2-7.4 (3H, m), 7.5-7.6 (2H, m), 8.42 (1H, dd, J=2 Hz, 9 Hz), 8.69 (1H, d, J=2 Hz), 9.18 (1H, s), 9.52 (1H, s).
IR (KBr) cm⁻¹: 3037, 2227, 1605, 1587, 1560, 1525, 1504, 1470, 1369, 1365, 1257, 1238, 1190, 1171.
FAB-MS (m/e): 331 (M+1)

Example 1

Action on BCRP-Mediated Methotrexate Transport (Testing Method)
In the experiment, plasma membrane was prepared from BCRP-expressing Sf9 cells. Its membrane vesicle was used (Ishikawa et al.: Methods of Enzymol., 400:485-510 (2005)).
The activity of methotrexate transport was measured using 96 wells-plate according to the following method.
Preparation and Composition of Reaction Solution
50 μL of solution containing sucrose (250 mmol/L) and Tris/Hepes (10 mmol/L, pH: 7.4)
30 μL of solution containing ATP (3.33 mmol/L), creatine phosphate (33.3 mmol/L), and MgCl₂ (33.3 mmol/L)
(or solution containing creatine phosphate (33.3 mmol/L) and MgCl₂ (33.3 mmol/L))
5 μL of creatine kinase (2 mg/mL)
2 μL of [³H]methotrexate (10 mmol/L, final concentration: 200 μmol/L)
3 μL of test compound
10 μL of membrane sample of BCRP-expressing Sf9 cells (total protein: 50 μg)
Total: 100 μL
The reaction solution was incubated at 37° C. for 20 minutes. 1 mL of ice-cooled solution containing sucrose (250 mmol/L), EDTA (2 mmol/L), and Tris/Hepes (10 mmol/L, pH: 7.4) was quickly added to the reaction solution to stop the reaction. Each 270 μL of the mixed solution was poured into each well of MultiScreen™ (Millipore), and sucked. The wells were washed four times with 200 μL of ice-cooled solution containing sucrose (250 mmol/L) and Tris/Hepes (10 mmol/L, pH: 7.4). The radioactivity trapped on a filter of each well was measured. The amount of methotrexate transported into the membrane vesicle was calculated from the radioactivity.
Further, the IC₅₀ value of the test compound [concentration inhibiting methotrexate transport by 50%, inhibitory concentration (μmol/L)] was obtained according to the above-mentioned method.

(Results)
As is shown in Table 1, it was confirmed that each of the compound 1 to 4, TMX-67, and FYX-051 strongly inhibits the BCRP-mediated methotrexate transport.

Action on BCRP-Mediated Methotrexate Transport

TABLE 1

| Test compound | IC₅₀ (μmol/L) |
| --- | --- |
| Compound 1 | 0.46 |
| Compound 2 | 1.1 |
| Compound 3 | 0.23 |
| Compound 4 | 0.66 |
| TMX-67 | 0.25 |
| FYX-051 | 0.77 |

Compound 1: Potassium salt of 2-[3-cyano-4-(4-fluorophenoxy)phenyl]-4-hydroxythiazolo[5,4-d]pyrimidine
Compound 2: 2-[3-Cyano-4-(4-fluorophenoxy)phenyl]thiazolo[5,4-d]pyrimidine
Compound 3 Potassium salt of 2-(3-cyano-4-phenoxyphenyl)-4-hydroxythiazolo[5,4-d]pyrimidine
Compound 4: 2-(3-cyano-4-phenoxyphenyl)thiazolo[5,4-d]pyrimidine

Comparison Example 1

Action on BCRP-Mediated Methotrexate Transport (Testing Method)

Action on BCRP-mediated methotrexate transport was tested with respect to allopurinol and oxypurinol in the same manner as in Example 1.

(Results)

Each of allopurinol and oxypurinol did not exhibit an inhibitory action even at concentration of 100 µmol/L.

Example 2

Influence on Anti-Cancer Agent Resistance in BCRP-Overexpressing Cells (Flp-In-293/BCRP)

(Testing Method)

Flp-In-293/ABCG2 cells and Flp-In-293/Mock cells were used in the experiment (Wakabayashi et al.: J. Exp. Ther. Oncol., 5:205-222 (2006)).

The cells were cultured under the atmosphere of 5% $CO_2$ using DMEM containing FCS (10%), penicillin (100 U/mL), streptomycin (100 µg/mL), amphotericin B (250 ng/mL), hygromycin B (100 µg/mL), and L-glutamine (2 mmol/L).

The resistance of Flp-In-293 cells to an agent was profiled by counting living cells using MTT assay. In more detail, the cells were seeded in 96-wells plate at the concentration of $2 \times 10^3$ cells/well, and cultured for 24 hours. SN-38 and the compound 1 (potassium salt of 2-[3-cyano-4-(4-fluorophenoxy)phenyl]-4-hydroxythiazolo[5,4-d]pyrimidine or compound 2 (2-[3-cyano-4-(4-fluorophenoxy)phenyl]thiazolo[5,4-d]pyrimidine) were added to the cells, and the cells were further incubated for 72 hours. The cells were treated with MTT (500 µg/mL), and were further incubated for 4 hours. Then the cells were treated with 100 µL of 10% SDS, and were incubated overnight. The formed MTT-formazan (metabolite of MTT, which is formed by living cells) was measured at the wavelength of 570 nm and 630 nm.

(Results)

Each of the compounds 1 and 2 reversed the resistance of Flp-In-293/ABCG2 cells to SN-38 in a concentration-dependent manner. The compound 1 reversed the resistance by about 96%, and the compound 2 reversed by about 90% at the concentration of 5 µmol/L. Further, the compounds did not affect viability of Flp-In-293/ABCG2 cells up to the examined concentration of 10 µmol/L.

Therefore, it has been confirmed that the compounds 1 and 2 do not exhibit toxicity to the cells, and do exhibit effect of overcoming anti-cancer agent resistance in the BCRP-overexpressing cells without exhibiting toxicity to the cells.

Example 3 and Comparison Example 2

Influence on Anti-Cancer Agent Resistance in BCRP-Overexpressing Cells (Flp-In-293/BCRP)

(Testing Method)

Influence on anti-cancer agent resistance in BCRP-overexpressing cells (Flp-In-293/BCRP) was tested in the same manner as in Example 2 with respect to 2-(3-cyano-4-phenoxyphenyl)-4-hydroxythiazolo[5,4-d]pyrimidine (compound 5), TMX-67, FYX-051, allopurinol, oxypurinol, and Y-700.

(Results)

(i) Degree of Overcoming Resistance to SN-38

The compound 5, TMX-67 and FYX-051 reversed the resistance by about 96%, about 82%, and about 39% respectively at the concentration of 5 µmol/L. On the other hand, allopurinol and oxypurinol did not exhibit an effect of overcoming resistance to SN-38. Further, Y-700 also did not exhibit an effect of overcoming the resistance in the concentration not exhibiting toxicity to the cells.

(ii) Toxicity to the Cells

The compound 5, TMX-67, FYX-051, allopurinol, and oxypurinol did not exhibit toxicity to the cells at the concentration of 10 µmol/L. Y-700 exhibits toxicity to the cells at the concentration of 5 µmol/L or higher.

What is claimed is:

1. A method for overcoming anti-cancer chemotherapeutic drug resistance comprising contacting a chemotherapeutic drug-resistant cell with an agent containing a compound having the following formula (I) or a salt thereof as an active ingredient for overcoming anti-cancer chemotherapeutic drug resistance:

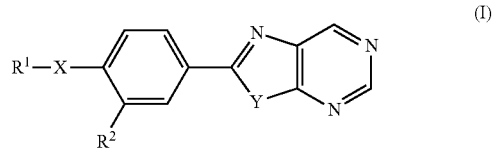

(I)

wherein $R^1$ is $C_{2-8}$ alkenyl, $C_{6-10}$ aryl, or heteroaryl in which the aryl and heteroaryl can have a substituent selected from the group consisting of $C_{1-8}$ alkyl, $C_{1-8}$ alkyl substituted with halogen, $C_{1-8}$ alkoxy, $C_{1-8}$ alkoxy substituted with halogen, $C_{2-8}$ alkoxycarbonyl, formyl, carboxyl, halogen, hydroxyl, nitro, cyano, amino, $C_{6-10}$ aryl, and $C_{6-10}$ aryloxy;

$R^2$ is cyano, nitro, formyl, carboxyl, carbamoyl, or $C_{2-8}$ alkoxycarbonyl;

X is oxygen, —N($R^3$)—, or —S(O)$_n$—, and $R^3$ is a hydrogen, $C_{1-8}$ alkyl, or the group mentioned above for $R^1$, or $R^1$ and $R^3$ are combined to form morpholinyl, thiomorpholinyl, or piperazinyl, and n is an integer of 0 to 2; and Y is oxygen, sulfur, or NH, wherein said drug-resistant cell over-expresses breast cancer resistance protein (BCRP).

2. A method for overcoming anti-cancer chemotherapeutic drug resistance comprising contacting a chemotherapeutic drug-resistant cell with an agent containing a compound having the following formula (II) or a salt thereof as an active ingredient for overcoming anti-cancer chemotherapeutic drug resistance:

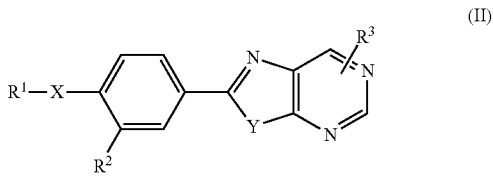

(II)

wherein $R^1$ is $C_{6-10}$ aryl or heteroaryl in which the aryl and heteroaryl can have a substituent selected from the group consisting of $C_{1-8}$ alkyl, $C_{1-8}$ alkyl substituted with halogen, $C_{1-8}$ alkoxy, $C_{1-8}$ alkoxy substituted with $C_{1-8}$ alkoxy, $C_{2-8}$ alkoxycarbonyl, formyl, carboxyl, halogen, hydroxyl, nitro, cyano, amino, $C_{6-10}$ aryl, and $C_{6-10}$ aryloxy;

$R^2$ is cyano, nitro, formyl, carboxyl, carbamoyl, or $C_{2-8}$ alkoxycarbonyl;

$R^3$ is hydroxyl, amino, carboxyl, mercapto, $OR^4$, or $NHR^5$, and each of $R^4$ and $R^5$ is $C_{1-8}$ alkyl or $C_{1-8}$ alkyl substituted with a group or atom selected from the group consisting of halogen, hydroxyl, nitro, cyano, amino, $C_{6-10}$ aryl, and $C_{6-10}$ aryloxy; X is oxygen, —N($R^6$)—, or —S(O)$_n$—, and $R^6$ is a hydrogen, $C_{1-8}$ alkyl, or the group mentioned above for $R^1$, and n is an integer of 0 to 2; and Y is oxygen or sulfur, wherein said drug-resistant cell over-expresses breast cancer resistance protein (BCRP).

3. A method for overcoming anti-cancer chemotherapeutic drug resistance comprising contacting a chemotherapeutic drug-resistant cell with a compound selected from the group consisting of 2-(3-cyano-4-phenoxyphenyl)-4-hydroxythiazolo[5,4-d]pyrimidine and potassium salt of 2-(3-cyano-4-phenoxyphenyl)-4-hydroxythiazolo[5,4-d]pyrimidine as an active ingredient for overcoming anti-cancer drug resistance, wherein said drug-resistant cell over-expresses breast cancer resistance protein (BCRP).

4. A method for overcoming anti-cancer drug resistance comprising contacting an anti-cancer drug-resistant cell with an agent containing Febuxostat or 4-[5-pyridin-4-yl-1H-[1,2,4]triazol-3-yl]pyridine-2-carbonitrile as an active ingredient for overcoming resistance to an anti-cancer drug, wherein said drug-resistant cell over-expresses breast cancer resistance protein (BCRP).

5. A method for overcoming multidrug resistance to anti-cancer drugs comprising contacting a multidrug-resistant cell with a therapeutic composition comprising an anti-cancer drug and a compound selected from the group consisting of 2-(3-cyano-4-phenoxyphenyl)-4-hydroxythiazolo[5,4-d]pyrimidine and potassium salt of 2-(3-cyano-4-phenoxyphenyl)-4-hydroxythiazolo[5,4-d]pyrimidine, wherein said drug-resistant cell over-expresses breast cancer resistance protein (BCRP).

6. A method for overcoming resistance to an anti-cancer drug comprising contacting an anti-cancer drug-resistant cell with an agent defined in any one of claim 1,2,3 or 4, wherein the agent is used except for treating hyperurcemia caused by tumor lysis.

7. A method of using a therapeutic composition defined in claim 5, wherein the therapeutic composition is used except for treating tumor lysis-induced hyperurcemia.

* * * * *